United States Patent
Pohjonen et al.

(10) Patent No.: US 6,503,278 B1
(45) Date of Patent: *Jan. 7, 2003

(54) UNDER TISSUE CONDITIONS DEGRADABLE MATERIAL AND A METHOD FOR ITS MANUFACTURING

(75) Inventors: Timo Pohjonen, Tampere (FI); Pertti Törmälä, Tampere (FI)

(73) Assignee: Bionx Implants Oy, Tampere (FI)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/043,720

(22) PCT Filed: Sep. 27, 1996

(86) PCT No.: PCT/FI96/00511

§ 371 (c)(1),
(2), (4) Date: Aug. 26, 1998

(87) PCT Pub. No.: WO97/11725

PCT Pub. Date: Apr. 3, 1997

(30) Foreign Application Priority Data

Sep. 27, 1995 (FI) ................................. 954566

(51) Int. Cl.[7] .................................. A61F 2/28
(52) U.S. Cl. ................ 623/16.11; 623/11.11; 623/23.51; 623/23.58; 623/23.75
(58) Field of Search ............ 623/11, 16, 11.11, 623/16.11, 23.51, 23.58, 23.61, 23.75

(56) References Cited

U.S. PATENT DOCUMENTS

| 4,304,767 A | 12/1981 | Heller et al. |
| 4,671,280 A | 6/1987 | Dorband et al. |
| 4,743,257 A | 5/1988 | Törmälä et al. |
| 4,968,317 A | 11/1990 | Törmälä et al. |
| 5,059,211 A | 10/1991 | Stack et al. |
| 5,084,051 A | 1/1992 | Törmälä et al. |
| 5,207,679 A | 5/1993 | Li |
| 5,411,523 A | 5/1995 | Goble |

FOREIGN PATENT DOCUMENTS

| EP | 0 321 176 B1 | 6/1989 |
| EP | 0 634 152 A1 | 1/1995 |
| FI | 863573 | 3/1988 |
| FI | 883197 | 1/1990 |
| FI | 885164 | 5/1990 |
| FI | 885981 | 6/1990 |
| FI | 891973 | 10/1990 |
| WO | WO 88 05312 | 7/1988 |
| WO | WO 90/04982 | 5/1990 |
| WO | WO 90 12550 | 11/1990 |
| WO | WO 93/14705 | 8/1993 |
| WO | WO 93/14706 | 8/1993 |
| WO | WO 95 26762 | 10/1995 |
| WO | WO 97/11725 | 4/1997 |

OTHER PUBLICATIONS

J. Brandrup et al. Entry from Kunststoff Lexikon (Dictionary of Plastics) 8th updated and expanded edition. pp. 324–325 (with English language translation).

E. W. Fischer, et al., "Investigation of the structure of solution grown crystals of lactide copolymers by means of chemical reactions", *Kolloid–Z.u.Z Polymere*, vol. 251, pp. 980–990., (1973).

(List continued on next page.)

Primary Examiner—Dinh X. Nguyen
(74) Attorney, Agent, or Firm—Kenyon & Kenyon

(57) ABSTRACT

This invention relates to a material that degrades after implantation into a patient's tissue, and resorbs into the patient's body, which material is manufactured of polymer, copolymer or polymer alloy. The material has a non-crystalline, i.e., amorphous structure and is molecularly oriented and reinforced by mechanical deformation. Further, the material can be formed into surgical devices, such as screws and pins, for implantation into a patient.

23 Claims, 5 Drawing Sheets

OTHER PUBLICATIONS

Figure 1:
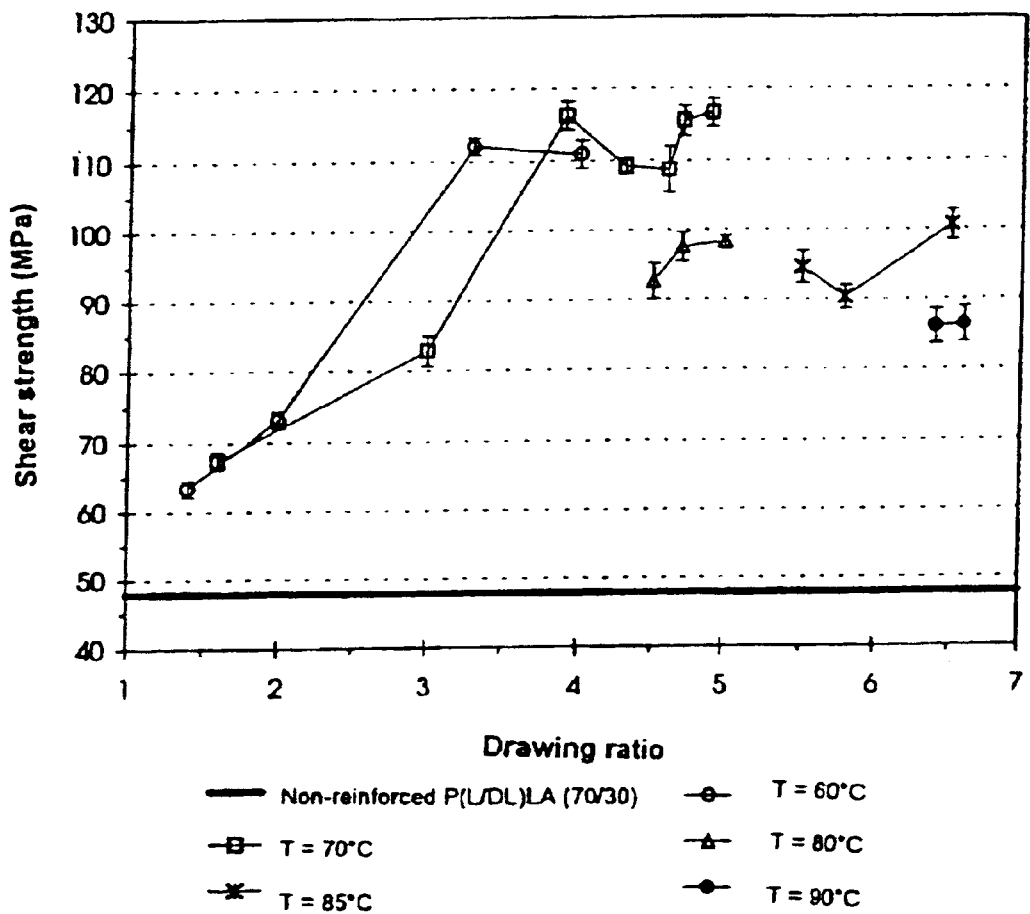

S. Vainionpaa, et al., "Surgical Applications of Biodegradable Polymers in Human Tissues" *Progress in Polymer Science*, vol. 14 No. 5, pp. 679–716 (1989).

P. Tormala, et al. "Ultra–high–strength absorbable self–reinforced polyglycolide (SR–PGA) composite rods for internal fixation of bone fractures: In vitro and in vivo study" *Journal of Biomedical Materials Research*, vol. 25, No. 1, pp. 1–22, (1991).

P. Tormala, et al. "Biodegradable Self–Reinforced Composite Materials; Manufacturing Structure and Mechanical Properties" *Clinical Materials*, vol. 10, pp. 29–34, (1992).

P. Rokkanen, et al., "Utilization of biodegradable implants in the surgical treatment of fractures and osteotomies", *Orthopedie Traumatologie*, vol. 2, pp. 107–110—Summary in English.

E. K. Partio, "The use of plaster cast or early mobilization of ankle fractures with absorbable screws" *Unfallchirurgie*, vol. 18, pp. 304–310 (1992)—Abstract in English.

H. Pihlajamaki, et al., "Absorbable Pins of Self–Reinforced Poly–L–Lactic Acid For Fixation Of Fractures And Osteotomies" *The Journal of Bone and Joint Surgery* vol. 74 B, No. 6, pp. 853–857 (Nov. 1992).

Y. Matsusue, et al., "In Vitro and in Vivo studies on bioabsorbable ultra–high–strength poly(L–lactide)rods" *Journal of Biomedical Materials Research*, vol. 26, No. 12, pp. 1553–1567 (Dec. 1992).

E. J. Bergsma, et al., "Foreign Body Reactions to Resorbable Poly(L–Lactide) Bone Plates and Screws Used for the Fixation of Unstable Zygomatic Fractures" *Journal of Oral and Maxillofacial Surgery*, vol. 51, No. 6, pp. 666–670 (Jun. 1993).

K.E. Rehm, et al., "Report on the working group on biodegradable implants" *Akutelle Traumatologie*, vol. 24, pp. 70–74 (Apr. 1994)—Abstract in English.

M. Talja, et al., "Biodegradable Self–Reinforced Polyglycolic Acid Spiral Stent In Prevention of Postoperative Urinary Retention After Visual Laser Ablation of the Prostate–Laser Prostatectomy" *The Journal of Urology*, vol. 154, No. 6, pp. 2089–2092 (Dec. 1995).

S. I. Ertel, et al., "Evaluation of poly(DTH carbonate), a tyrosine–derived degradable polymer, for orthopedic applications" *Journal of Biomedical Materials Research*, vol. 29, No. 11, pp. 1337–1348 (Nov. 1995).

T. Yamamuro, et al., "Bioabsorbable osteosynthetic implants of ultra high strength poly–L–lactide" *International Orthopaedics*, vol. 18, No. 6, pp. 332–340 (1994).

Textbook of Fred W. Billmeyer, Jr., Polymer Science, Wiley International Edition 1962, Structure and Properties of Polymers, 170–171.

Die Angewandte Makmolekulare Chemie 166/167 (1989) 155–168 (2786) Bioresorbable Polymers for Temporary Therapeutic Applications.

Journal of Applied Biomaterials, vol. I, 57–78 (1990), Mechanical Properties of Biodegradable Polymers and Composites Proposed for Internal Fixation of Bone.

Journal of Biomedical Materials Research, vol. 28, 919–930 (1994), Evaluation of a series of tyrosine–derived polycarbonates as degradable biomaterials.

UNDER TISSUE CONDITIONS DEGRADABLE MATERIAL AND A METHOD FOR ITS MANUFACTURING

The invention relates to under tissue conditions degradable material.

In surgery, it is known to employ implants manufactured of biodegradable (under tissue conditions absorbable) polymers for connecting tissues together, for separating tissues from each other, for temporarily replacing tissues partially or entirely and for guiding the healing or growth of the tissues. It is known to manufacture of partly crystallized thermoplastic, biodegradable polymers strong implant materials by stretching elongated blanks, such as fibres or bars in a manner that the crystalline structure of the materials is modified and directed (oriented) increasing the strength and the stiffness of the material in the orientation direction. Publication U.S. Pat. No. 4,968,317 presents partly crystalline, biodegradable biomaterials, oriented by the drawing technique which can be used when manufacturing e.g. various equipments for fixation of bone fractures. Publication EP-03211761 presents a method for manufacturing oriented, partially crystalline, biodegradable material by cooling the thermoplastic polymer to a temperature lower than its glass-transition temperature, in which the nucleation of the crystals takes place, and by reheating the material to a temperature which is higher than the glass-transition temperature of the material but lower than its melting temperature, and by stretching the material under these conditions to gain orientation.

Publication WPI ACC No: 89-220470/30 presents a surgical biomaterial consisting of molecularly oriented lactic acid polymers or its copolymer with glycol acid, having a crystal content of 10 to 60% in the material and a compression bending strength of 160 to 250 MPa.

Partially crystalline biodegradable polymer materials can be used for manufacturing e.g. various rods, screws, plates etc. to be employed e.g. when repairing bone fractures or damages in connective tissue. The following publications disclose results of applying these types of materials in surgical use: P. Rokkanen et al.: "Utilisation des implants biodegradables dans le traitement chirurgical des fractures et au cours des ostéotomies", Orthop. Traumato 12, (1992), pp. 107–11; E. K. Partio et al.: "Immobilisierung und Fr ühmobilisierung von Malleolarfrak-turen nach Osteosynthese mit resorbierbaren Schrauben", Unfall-chirurgie 18(5), (1992), pp. 304–310; H. Pihlaiamäki et al.: "Absorbable pins of self-reinforced poly-l-lactic acid for fixation of fractures and osteotomies", J Bone Joint Surg 74-B(6), (1992), pp. 853–857; T. Yamamuro et al.: "Bioabsorbable osteosynthetic implants of ultra high strength poly-L-lactide. A clinical study", Int. Orthop. 18, (1994), pp. 332–340.

Crystalline configuration as such gives the non-oriented biodegradable materials strength and toughness in a manner that they can be employed e.g. in bone surgery, in selected surgical embodiments, such as in healing of non-loaded bone fractures (cf. e.g. S. Vainionpää, P. Rok-kanen and P. T örmälä: "Surgical applications of biodegradable polymers in human tissues", Prog. Polym. Sci. 14, (1989), pp. 679–716).

Although the partially crystalline biodegradable materials have good, in case of oriented materials even excellent, strength properties, and the strength retention time in vivo can be controlled to a typical term of 1 to 12 months, the disadvantage is very slow degrading of the crystal phase of the material. Numerous researches have found out that partially crystalline, biodegradable materials first degrade at their amorphous (noncrystalline) parts, since degrading starts and is easiest in the amorphous areas of the material, which are situated between the crystalline areas (cf. e.g. E. W. Fischer, H. J. Sterzel, G. Wegner G.: "Investigation of the structure of solution grown crystals of lactide copolymers by means of chemical reactions". Kolloid-Z. Polym. 251, (1973), pp. 980–990). As a result of the said heterogeneous degradation, in the last phase of the polymer absorbing, mainly crystalline, very slowly degradable particles are created. In some tissues, these particles can cause harmful side effects, such as swelling in the tissue and pain (cf. e.g. E. J. Bergsma et al.: "Foreign Body Reactions to Resorbable Poly (L-lactide) Bone Plates and Screws Used for the Fixation of Unstable Zygomatic Fractures", J. Oral Maxillofac. Surg. 51, (1993) pp. 666–670).

However, since the non-crystalline (amorphous) biodegradable polymer material has no slowly degradable crystal structures, degradation of amorphous polymer is under tissue conditions faster than degradation of partially crystalline polymer, and due to the lack of crystalline structure, no such harmful tissue reactions can occur when the amorphous polymers are degrading, as described e.g. in the above mentioned publication E. J. Bergsma et al. However, a drawback with amorphous biodegradable polymers is their poor mechanical strength properties. As for the mechanical properties, the amorphous biodegradable materials are either very ductile ("rubber-like"), if their glass-transition temperature is under the body temperature, or, on the other hand, they are hard and glass-like it their glass-transition temperature is over the body temperature. In every case, the amorphous polymers have relatively weak strength properties.

Insufficient strength of the amorphous, biodegradable polymer implants is found in clinical research as high frequency of breaking of fracture fixations. E.g. the publication K. E. Rehm, H.-J Helling, L. Claes: "Bericht der Arbeitsgruppe Biodegradable Implante", Akt. Traumatol. 24 (1994), pp. 70–74 presents clinical results from 57 patients. In the research, various fractures in the cancellous bone area were fixated with biodegradable rods manufactured of amorphous poly-L/DL-lactide (with L/DL ratio of 70/30). In the post-surgical follow-up of the patients, a dislocation of bone fragment was noticed in tour patients, which signifies fies that this complication was found in 7% of the patients. Further, with two patients (3.5 % of the patients) dislocation of the rod head was found. Thus, the total proportion of complications was high: 10.5%. Dislocation of bone fragment and dislocation of rod head show that the strength of the amorphous lactide copolymer, particularly the shear strength, was not sufficient for providing safe healing. This result differs clearly e.g. from the clinical research of H. Pihlajamäki et al.: "Absorbable pins of self-reinforced poly-L-lactic acid for fixation of fractures and osteotomies", J. Bone Joint Surg. (Br) Vol. 74-B, (1992), pp. 853–357, using rods of a corresponding type for the fixation of fractures and osteotomies in cancellous bone area, which rods were manufactured of partly crystalline, oriented (self-reinforced) poly-L-lactide. The research comprised 27 fixation-operated patients, in whom no bone fragment dislocations or rod dislocations were found in the post-operation follow-up (8 to 37 months); i.e. the degree of complications was 0%. Since the shear strength of partially crystalline, oriented polylactide rods is more than double compared to that of amorphous, non-oriented polylactide rods (the shear strength of rods used by Pihla-jamäki et al. was 100 to 180 MPa and the shear strength of rods used by Rehm et al. was measured 46 to 54 MPa, cf. Example 1), it is obvious that the high proportion of complications in the research of Rehm et al. was due to insufficient strength properties of the material used in their study. On the other hand, since no slow-absorbtion, crystalline phase is present in the amorphous polymer, absorbing of the amorphous polymer takes place, after loosing the strength, faster than absorbtion of partly crystalline polymer. For example according to the publication of Rehm et al., rods manufactured of amorphous poly-L/DL-lactide were absorbed almost entirely in two years under tissue conditions, whereas according to Bergsma et al., there was a significant quantity of crystalline poly-L-lactide present at the operation site in the patient even after three years and eight months after the implantation. Also Y. Matsususe et al. ("In vitro and in vivo studies on bioabsorbable ultra-high-rigidity poly(L-lactide) rods, J. Biomed. Mater. Res. 26, (1992), pp. 1553–1567) noticed that 18 months after the placing of the implant, a significant amount (−30 %) of partly crystalline poly-L-lactide remained in the laboratory animals.

Since the biodegradable implant becomes useless in the patients system after having lost its strength, it would be advantageous that the implant would absorb as soon as possible after loosing its strength.

Thus, crystalline nature gives the biodegradable material its good initial strength, but it retards the final absorbtion of the polymer after the material has lost its strength, and it may even cause harmful chronic complications in certain embodiments. The amorphous material, in its turn, absorbs last but causes the patient risks when healing (danger of dislocation), because of its poor mechanical properties.

It has been surprisingly discovered in this invention that the drawbacks of known partly crystalline and, on the other hand amorphous biodegradable surgical implants can be efficiently eliminated by using in their manufacturing, instead of known materials, amorphous, biodegradable polymer, copolymer or polymer combination oriented and reinforced (self-reinforced) by means of draw technique. The present invention thus presents molecularly oriented, self-reinforced, amorphous, biodegradable surgical biomaterials, their use in the manufacturing of surgical implants, their parts or compounds, and surgical implants, their parts or compounds manufactured of said biomaterials. Said biomaterials and implants manufactured thereof can be used in surgery for connecting together tissues or parts thereof, for separating tissues or parts thereof, for temporarily replacing tissues and/or for guiding healing or growth of tissues. The self-reinforced materials and implants in accordance with the invention surprisingly combine the advantageous prop eties of known biodegradable, partially crystalline and, on the other hand amorphous materials, and simultaneously eliminate the draw-backs of the materials. Materials of the invention have surprisingly an especially good shear strength, they are tough, they retain their strength for long (typically several months in vivo), when slowly degradable polymer is used as raw material, and after having lost their strength they absorb faster than known strong, partly crystalline, corresponding biodegradable biomaterials. When tested, reinforcing can be seen as an increase of the strength values in the entire macroscopic piece. Additionally, materials of the invention can be sterilized by γ-radiation without them loosing too much of their advantageous properties.

To obtain the above mentioned objects, under tissue conditions degradable material according to the invention is mainly characterized by what is said in the characterizing part of the accompanying independent claim 1.

The materials according to the invention have proved out to be surprisingly strong and tough in a manner that they can be used in manufacturing various surgical implants to connect tissues or parts thereof to each other, to separate tissues or parts thereof from each other, to temporarily replace tissues and/or to guide healing or growth of tissues. Implants of this type include e.g. various rods, screws, pins, hooks, intramedullary nails, plates, bolts, suture anchors, foils, wires, tubes, stents, spirals or implants of a corresponding type, presented e.g. in publications U.S. Pat. No. 4,743,257, FI Pat. No. 81010, U.S. Pat. No. 4,968,317, FI Pat. No. 84137, FI Pat. No. 85223, FI Pat. No. 82805, PCT/FI 93100014 and PCT/FI93/00015, U.S. Pat. Nos. 5,084,051, 5,059,211, FI Pat. No. 88111 and EP-634152.

The materials of the invention can be manufactured of thermoplastic, amorphous biodegradable polymers, such as L-lactide copolymers containing a large quantity of D-lactide units (e.g. poly L/DL-lactides having 15 to 85 molecular-% of D-units), amorphous copolymers of lactide and glycol, as well as polymer combinations forming amorphous alloys. It is self-evident that the materials of the invention can be manufactured also from other amorphous, biodegradable polymers, like e.g. of polyorthoesters, (see e.g. U.S. Pat. No. 4,304,767), of pseudopoly (amino acids) (see e.g. S. I. Ertel et al., J. Biomed.Mater. Res., 29 (1995) pp. 1337–1378), etc.

Further, materials in accordance with the invention can include as compound agent powder-like ceramic or corresponding materials. such as bone meal, hydroxyl-apatite powder, calcium-phosphate powder and other absorbable ceramic powders or absorbable ceramic fibres, like bioglass fibres.

According to one advantageous embodiment, the material of the invention also contains at least one organic or inorganic bioactive agent or agents, such as antibiotics, chemotherapeutic agents, agents activating the healing of wounds (e.g. angiogenic growth factors), bone growth factors (bone morphogenic proteins [BMPD] etc. Such bioactive materials are particularly advantageous in clinical use, since, in addition to mechanical effect, they also have biochemical, medical and other effects for tissue healing.

It is obvious that the materials of the invention can also include various additives for facilitating processing of the material (e.g. stabilizers, anti-oxidants or softeners) or for altering its properties (e.g. softeners or powder-like ceramic materials or biostable fibres, such as polyaramid or carbon fibres) or for facilitating its handling (e.g. colorants).

The accompanying dependent claims present some advantageous embodiments of the material according to the invention.

The invention also relates to a method for manufacturing under tissue conditions absorbable material. The method is mainly characterized by features presented in the characterizing part of the accompanying independent claim relating to the method.

Advantageous embodiments of the method are presented in the accompanying independent claims.

When manufacturing materials in accordance with the invention, a molecular orientation is carried out by modifying biomaterial in solid state mechanically in a temperature where large scale molecular movements are possible, but where thermal movement is not strong enough for the achieved orientation to relax as a result from the molecular thermal movements.

The simplest way of performing the mechanical modification is to draw a melt-processed (such as injection molded, extrusion molded or compression molded), non-oriented billet or preform (such as a rod, plate or film) to a typical drawing ratio of 2 to 6 in the direction of the longitudinal axis of the billet. The drawing can also be carried out as a so called die drawing, wherein the billet is drawn through heated die to a suitable drawing ratio. As a result of the drawing, the molecule chains and/or parts thereof are directed increasingly to the draw direction, wherein the strength and toughness of the material are growing in the draw direction. After the drawing, the drawn billet is cooled under stress to room temperature, and various implants can be further processed thereof, such as rods, screws, plates, pins, hooks, stents, spirals etc. Suitable processing methods are e.g. turning, milling, shearing and other mechanical processing methods, thermal processing (compression molding under heat and pressure) or combinations of mechanical processing and thermal processing.

During drawing, the billet or die can also be turned around the longitudinal axis of the billet, wherein a spiral orientation is obtained thereto, which is particularly advantageous e.g. in screws.

For plate-formed and foillike preforms, also two-axial drawing can be carried out, wherein orientation is obtained for the billet also in a direction perpendicular to its longitudinal axis.

Materials of the invention can be manufactured of said raw materials also by using so-called solvent methods, wherein at least a part of the polymer is solved into a suitable solvent or softened by the solvent and the material or the material combination is compressed to a piece by using pressure and possibly a slight heat, wherein the solved or softened polymer glues the material to a macroscopic piece, from which the solvent is eliminated by evaporating. Techniques of this type are suitable particularly when manufacturing thermosensitive enzymes, peptides and proteins, such as implants containing BMP-molecules.

Figure 2:
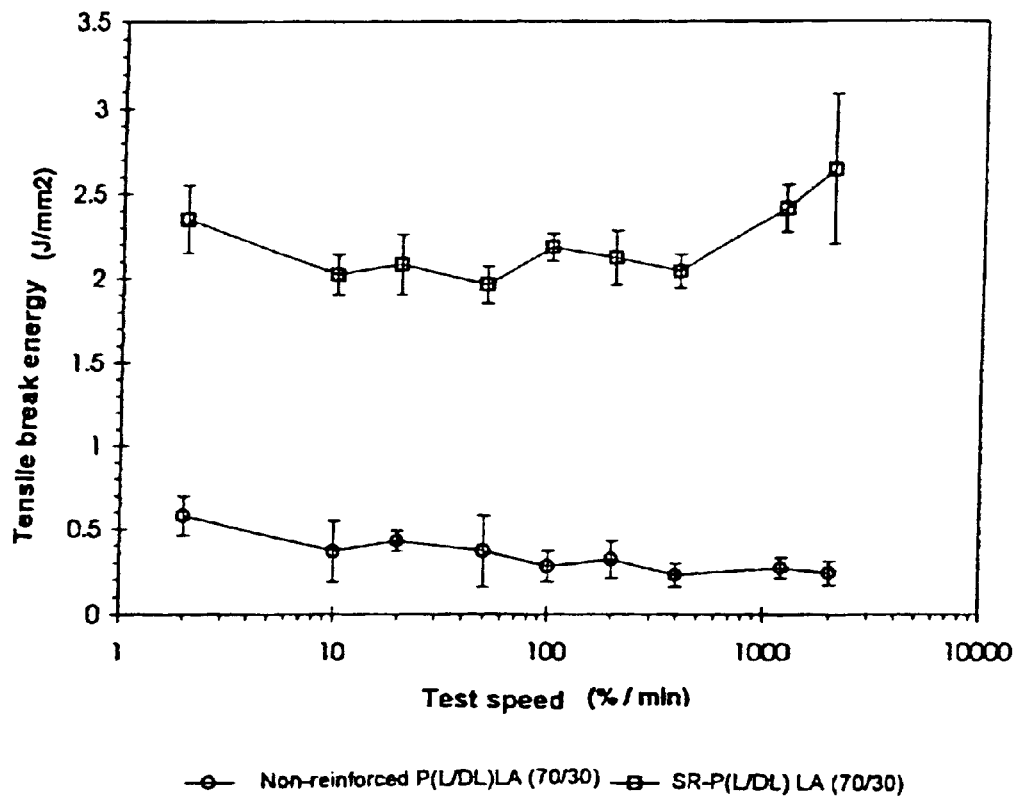

In the following specification, the invention is illustrated with reference to the Examples and the accompanying drawings. In the drawings FIG. 1. shows test results in drawing ratio—shear strength-co-ordination according to Example 1, FIG. 2 shows test results in test speed—tensile break energy-co-ordination according to Example 1.

Figure 3:
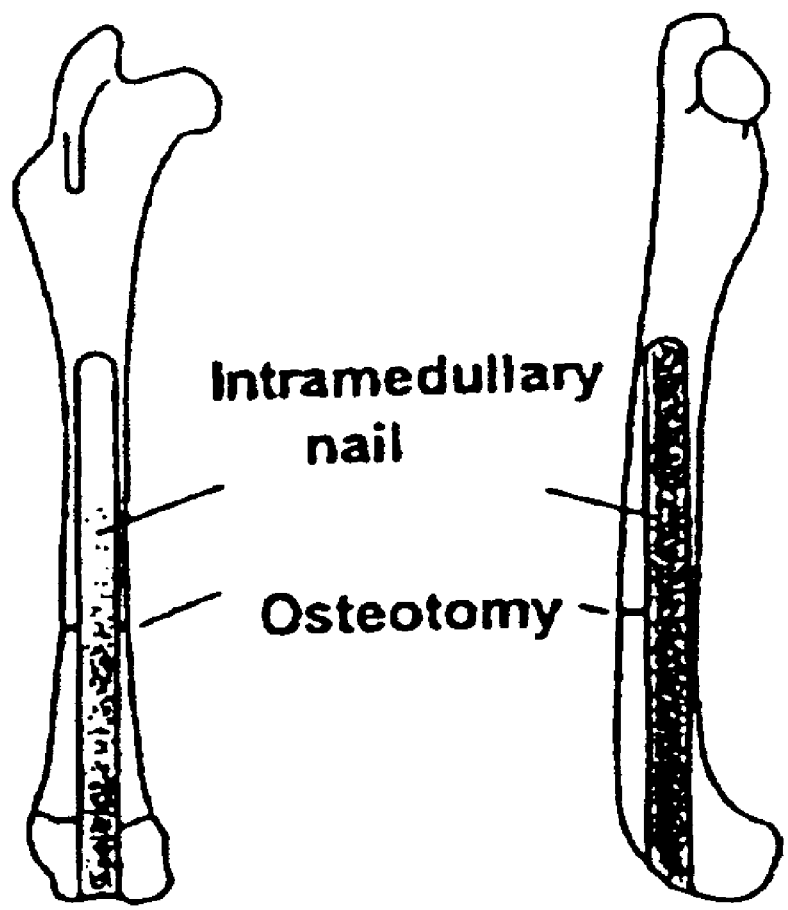
Figure 4A:
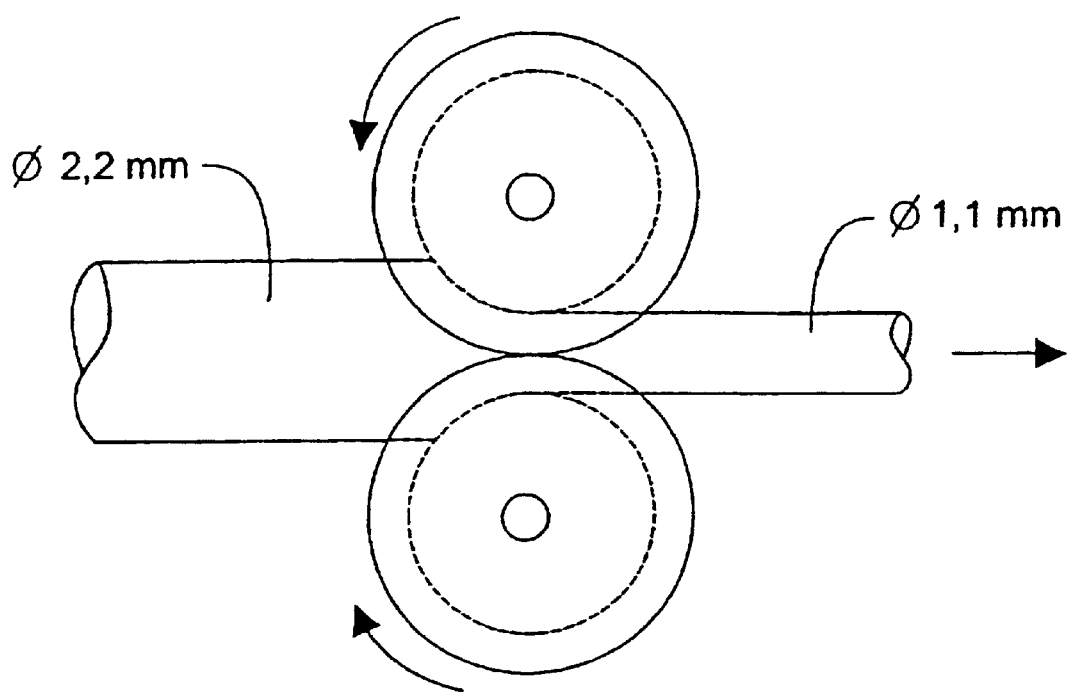
Figure 4B:
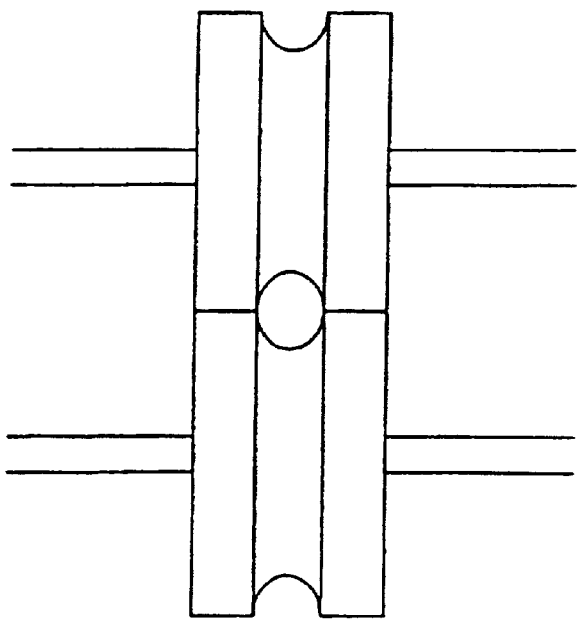
Figure 5:
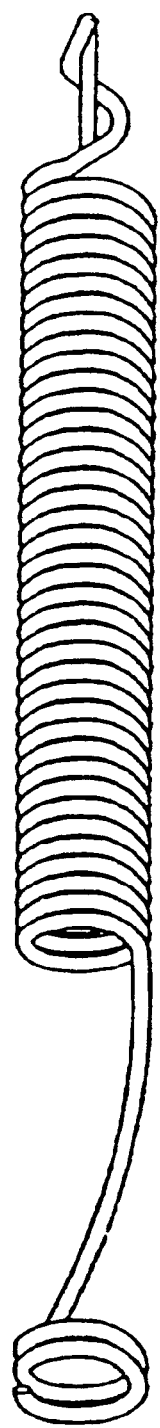

FIG. 3 shows from two directions the installation of intramedullary nails in connection with osteotomy in a femur according to Example 3, FIG. 4 shows from the side (4a) and from the front (4b) the manufacturing of material billet according to Example 8, and FIG. 5 shows a perspective view of a prostate spiral manufactured of a billet according to FIG. 4.

EXAMPLE 1

Cylindrical billets having a diameter of 2, 3, 4 and 5 mm were manufactured of poly-L/DL-lactide (L/DL mole ratio 70/30, incl. viscose 5.8 dl/g, trade name Resomer® LR708, manufacturer Boehringer Ingelheim, Germany) by extrusion (1-screw extruder), which billets were cooled to room temperature.

Shear strength was measured according to a method presented in the publication P. Törmälä et al.: "Ultra-high rigidity absorbable self-reinforced polyglycolide (SR-PGA) composite rods for internal fixation of bone fractures": In vitro and in vivo study" J. Biomed. Mat. Res., 25 (1991), pp. 1–22 to a billet having a diameter (Ø) of 2 mm. The obtained shear strength value was 50±4 MPa.

Billets of various sizes were drawn at various temperatures to various drawing ratios (to rods of Ø 2 mm) for obtaining at least a partial molecular orientation and for improving the shear strength of the material. The shear strengths of rods oriented and reinforced by drawing are presented in FIG. 1. According to FIG. 1, even with a drawing ratio 2 the shear strength of the rod has increased to 1.5-fold (to a value of 73 MPa) as compared to a non-drawn rod. With drawing ratios 3 to 5, shear strengths of 110 to 118 MPa are obtained, which values are already in the same area as the values measured for partially crystalline, drawn polylactide rods (cf. e.g. S. Vainionpää et al.: Surgical applications of biodegradable polymers in human tissues", Prog. Polym. Sci. 14, (1989), pp. 679–716).

Bending impact toughness of a non-drawn P(L/DL)LA (70/3) rod and a rod of the same material drawn to a drawing ratio 5 at a temperature of 70° C. were tested at a room temperature by defining the bending impact energy (J/mm$^2$) of the rods (both having a diameter of 2 mm) by a three-point bending-impact machine. The bending impact energy required for breaking the non-drawn rod was 0.017 J/mm$^2$ and the rod was broken in a brittle manner. The drawn rod did not break at all, but it bent in a ductile manner and glided through the supports of the measuring equipment when the bending impact energy value was 0.093 J/mm$^2$.

Thus, as a result of the drawing reinforcement, the bending behaviour of the amorphous Resomer® LR 708 polymer in impact stress changed from brittle to ductile and the endurance of the bending impact of the material increased more than five fold.

Corresponding break toughness tests were made to a non-drawn and drawn P(L/DL)LA (70/30) rods (Ø 2 mm) (drawing ratio about 5, draw temperature 75° C.) at a room temperature by measuring the energy needed for breaking the rod in a drawing test as a function of the testing speed (%/min.). The results are shown in FIG. 2. According to FIG. 2, the tensile break energy of non-drawn rods is between 0.2 to 0.7 J/mm$^2$, whereas the tensile break energy of drawn rods was between 1.8 and 3 J/mM$^2$. Depending on the test conditions, the tensile break energy of the material thus increased to 2.5 fold (slow draw)—15 fold (impact draw) as a result of the draw reinforcing.

EXAMPLE 2

Drawn (self-reinforced) P(L/DL)LA (70/30) rods (length 30 to 50 mm, thickness 2 mm) according to Example 1 were dried in a vacuum at a temperature of 37° C. for several days. The rods were packed in Al-foil bags and sterilized with γ-radiation (dose 2.5 Mrad.)

Clinical research, corresponding to the research of K. E. Rehm et al.: "Bericht der Arbeitsgruppe Biodegradable Implantate", Akt. Traumatol 24, (1994), pp. 70–74, was performed relating to the use of drawn, γ-sterilized, self-reinforced SR-PLA rods (L/DL ratio 70/30) for fixation of fractures in cancellous bone area. Table 1 contains comparison between indication groups of the Rehm et al. research (using non-oriented, reinforced P(L/DL)LA (70/30) rods, Ø 2 mm) and indication groups of the accompanying clinical research (using oriented and self-reinforced P(L/DL)LA (70/30) rods; Biofix® SR-PLA, Ø 2 mm). In the clinical research of the rods according to the invention, attempts were made to reach as good correspondence as possible with the research of Rehm et al.

TABLE 1

Indication groups in the clinical research of non-reinforced P(L/DL)LA (70/30) rods, (Rehm et al: Polypin ®) and self-reinforced P(L/DL)LA (70/30) rods, (Biofix ® SR-PLA)

| Indications | Polypin ® | Biofix ® SR-PLA |
|---|---|---|
| Apical fractures | 37 patients | 40 patients |
| Osteochondral fractures | 9 patients | 12 patients |
| Non-loaded cancellous bone fractures | 8 patients | 6 patients |
| Others | 3 patients | 4 patients |
| TOTAL | 57 patients | 62 patients |
| COMPLICATIONS: | | |
| Fracture dislocations | 4 (7%) | 1 (1.6%) |
| Rod head dislocations | 2 (3.5%) | — |
| COMPLICATIONS TOTAL | 6 (10.5%) | 1 (1.6%) |

Table 1 shows that with non-reinforced Polypin® rods, there were more than a six-fold quantity of complications compared to clinical use of the self-reinforced Biofix® SR-PLA rods, having only one fracture dislocation (a severe fracture of radius head). Since the material used in both tests was chemically the same and the rods had the same diameter (2 mm), it is obvious that the shear strength of the self-reinforced Biofix® SR-PLA rods in accordance with the invention was more than twice as high (>100 MPa) as compared to the shear strength of Polypin® type material (about 50 MPa), which makes the Biofix® SR-PLA rods more suitable for clinical use.

EXAMPLE 3

Bar with thickness of 3 mm was manufactured of PDLLA polymer (L/D molecular ratio of 50/50), incl. viscosity 5.2 dl/g, trade name Purasorb® PLD, manufacturer PURAC Biochem, Holland) by melt processing with 1-screw extruder, which bar was then cooled to room temperature. The bar was drawn at a temperature of 60° C. to the drawing ratios of 3.3 and 5.5. The shear strengths of non-drawn and drawn bars were measured (Table 2).

TABLE 2

Self-reinforcing of PDLLA polymer by drawing

| Drawing ratio | Shear strength (MPa) |
|---|---|
| 5.5 | 50 ± 1 |
| 3.3 | 84–85 |
| 1 | 96 ± 4 |

According to Table 2, the shear strength of the amorphous PDLLA increased almost to double when the material was drawn to a drawing ratio 5.5.

Non-drawn (non-reinforced) SR-PDLLA rods and corresponding drawn rods (self-reinforced) drawn to a drawing ratio of 5.5 were manufactured. The length of the rods was 50 to 60 mm, and the diameter was 4.5 mm.

20 adult rabbits were killed and the right femora were taken to biomechanical research. Holes of 4.5 mm were drilled to the intramedullary canal from the intercondylar area and the intramedullary canals were expanded with a rasp to the diameter of 4.5 mm. Osteotomy was made by a rotating diamond drill in the distal third of the diaphysis area in the femora. The osteotomy was fixated by using either a non-reinforced 4.5×(50–60) mm rod or a self-reinforced 4.5×(50–60) mm rod as the intramedullary nail (FIG. 3).

Bending rigidities of the sheared femora nailed with intramedullary nails were measured by using a 3-point bending test. The femora having self-reinforced rods as intramedullaty nails had circa twice as good bending rigidities compared to femora having non-reinforced rods. On the basis of these results it was concluded that self-reinforced SR-PDLLA rods are more suitable for intramedullary nails of bone fractures than non-reinforced ones.

EXAMPLE 4

SR-PLA rods in accordance with Example 2 were manufactured (drawing ratio 5.5, rod length 70 to 200 mm, diameter 2 mm), which rods were γ-sterilized (radiation dose=2.5 Mrad).

The rods were used as intramedullary nails for fixation of fractures of cortical area in radii of ten children (ages 2 to 7 years), by using "stack pinning" technique (two or more rods were used for filling the intramedullary canal). After the nailing, a plaster immobilisation was used for six weeks.

All the ten fractures provided with intramedullary nails healed well or in a satisfactory manner.

EXAMPLE 5

According to Example 1, self-reinforced P(L/DL)LA (70/30) rods (drawing ratio=5) having a thickness of 2 mm, as well as non-reinforced rods of the corresponding size, were manufactured.

The rods were γ-sterilized (radiation dose=2.5 Mrad) and hydrolyzed in phosphate buffer solution (pH 7.4) at 37° C. for 40 weeks. After 20 weeks of hydrolysis, the bending strength of the self-reinforced rods was still the same as at the starting point (170±10 MPa), whereas the non-oriented rods had lost more than a half of their original strength (original bending strength 120 MPa, after 20 weeks of hydrolysis: 55 MPa).

The half-life of rigidity in said hydrolysis was 32 weeks with self-reinforced rods and only 19 weeks with non-reinforced rods.

The above mentioned tests showed that self-reinforcing of the amorphous material makes it more durable against γ-sterilisation than non-reinforced material, even to the extent that reinforced rods can be γ-sterilized for clinical use. This is a significant advantage for the patients, since in the alternative ethylene-oxide sterilisation harmful residues of ethylene oxide may be left in the material.

EXAMPLE 6

In accordance with Example 1, self-reinforced rods (diameter 2.5 mm, length 70 mm) were manufactured of extruded P(L/DL)LA (70/30) billet (diameter 5 mm) by drawing to the drawing ratio 4 at a temperature of 60 to 90° C. Plates having a thickness of 0.5 mm (width 10 mm, length 70 mm) were manufactured of draw-reinforced rods between heated steel plates by compression molding at a temperature of 60 to 90° C. Non-reinforced plates of the corresponding size were manufactured by extrusion (1-screw extruder) by using a flat-foil die.

The mechanical properties of the non-drawn and draw-reinforced and compressed plates were examined by draw and shear tests at a room temperature. The effect of drill holes to the rigidity of the plates was examined by drilling 6 holes (Ø 2.0 mm) in a part of the plates. Table 3 shows strength values of a plate drawn at 70° C. and compression molded at 90° C., as compared to a non-reinforced plate.

TABLE 3

Self-reinforcing of P(L/DL)LA (70/30) plates

| P(L/DL)LA (70/30) | Tensile strength intact plate (MPa) | Tensile strength holes drilled (MPa) | Shear strength intact plate (MPa) | Shear strength holes drilled (MPa) |
| --- | --- | --- | --- | --- |
| non-reinforced | 55 | 47 | 49 | 47 |
| reinforced | 134 | 110 | 90 | 85 |

According to Table 3, the drilling of holes deteriorated the tensile strength of the plates by 18%, but it did not have significant effect on the shear strength. Even after the drilling of holes, the strengths of the self-reinforced plates were 1.8 to 2.3 fold as compared to non-reinforced plates.

EXAMPLE 7

Self-reinforced (drawn) P(L/DL)LA (70/30) rods (length 35 mm) of Example 5 were implanted in the muscular tissue in the back of 20 adult rabbits. The rabbits were divided into four groups and after they were killed, biodegradation of the self-reinforced rods were examined under tissue conditions by histological methods after six months, one, two and three years from implantation. Six months after the implantation the shapes of the rods were almost unaltered, although two rods were broken into two or three pieces, presumably as an effect of muscular movement. One year after the implantation all the rods were broken into pieces. Two years after the implantation, the material was almost entirely absorbed; only some occasional polymer particles could be found in the muscular tissue. Three years after the implantation the polymer was entirely absorbed and disappeared from the tissues.

To provide comparison material, a corresponding series of test was carried out by implanting in the muscular tissue of the rabbits partially crystalline, self-reinforced poly-L-lactide rods (manufacturer of the material: PURAC Biochem, Holland, $M_w$=250 000) which were manufactured by self-reinforcing technique (drawing technique) (according to the method of the publication P. Törmälä: "Biodegradable self-reinforced composite materials: manufacturing, structure and mechanical properties, Clinical Materials", 10, (1992), pp. 29–34). The thickness of the rods was 2 mm and the length was 35 mm. In histological research it was noted that six months and one year after the implantation the rods were still unaltered. Two years after the implantation the rods were broken into several pieces and partially disintegrated. Three years after the implantation there were still a large quantity of disintegrated poly-L-lactide material (debris) to be found in the muscular tissue.

The present research proved that amorphous, self-reinforced implants in accordance with the invention absorb in tissues considerably faster than corresponding, partially crystalline, self-reinforced materials.

EXAMPLE 8

Oriented billet of diameter 1.1 mm was manufactured of P(L/DL)LA (70/30) material by draw-reinforcing technique, by drawing a blank having a diameter of 2 mm slowly through heated (T~80° C.) rollers in a manner shown in FIG. 4a. As shown in FIG. 4b, the surfaces of the rollers comprised grooves, which together formed a channel of 1.1 mm diameter between the rollers.

Prostate stents (spirals) according to FIG. 5 were manufactured of drawn billet in accordance with technique presented in publication WO 90/04982, to be used to eliminate urethral retention in the prostate area, after laser treatment for benign prostatic hyperplasia. Lengths of the cylindrical part of the stents were 55, 65, and 75 mm and the total lengths were about 80 to 100 mm.

A stent according to the invention was inserted in ten patients after laser treatment (VLAP-laserprostatectomy) for prostatic hyperplasia, according to the publication M. Talja et al.: "Biodegradable SR-PGA-uro-spiral in prevention of postoperative urinary retention after VLAP-laser prostatectomy", J Urol. (in press).

When using a prostate spiral according to the invention, there was no deteriorating of urine-flow velocity to been seen in the patients during the healing; the follow-up term was 12 months. The prostate spirals absorbed and left the urethra in a period of 3 to 9 months (found on the basis of endoscopical research).

According to the above mentioned publication M. Taija et al., when self-reinforced, partially crystalline polyglycolide (SR-PGA) prostate spirals were used as post-treatment of laser treatment for benign prostatic hyperplasia, in ten patients out of 22 deteriorated urine-flow velocity occurred temporarily about three weeks after the insertion of the spiral. This was presumably due to the absorbing of the spiral three to four weeks after the implantation.

This comparative clinical research showed that the SR-PLA spirals in accordance with the invention provided better treatment results in post-laser treatment for benign prostatic hyperplasia than prior art, partially crystalline, self-reinforced spirals.

EXAMPLE 9

According to Example 1, self-reinforced P(L/DL)LA (70/30) rods having a thickness of 2 mm (drawing ratio =5), as well as non-reinforced rods of the corresponding size were manufactured. The lengths of the rods were 20 mm. Both in self-reinforced and non-reinforced rods was made, by turning at one end for the length of 10 mm, a screw thread, having the minimum diameter of 1.5 mm, the maximum diameter of 1.8 mm and the distance of 0.8 mm between the peaks of the threads. The threaded rods were sharpened at their tops.

10 mm deep holes were drilled in the distal part of a cow femur in the cancellous bone area by using a 1.1 mm bone drill. Holes were threaded with a tapping device, having the same profile as the above mentioned, threaded rod parts. The threaded rods were screwed in the holes, made in the bones and having a thread profile, by fixating the rods at their smooth part in the socket of the drilling machine and by screwing the screw thread parts of the rods into the holes. Draw-out force of both self-reinforced and non-reinforced threaded rods were measured by fixating the socket of the drilling machine to a mechanical testing device and by drawing the threaded rod out of the bone. A relative draw-out force was determined to the self-reinforced rods in a following manner:

$$\text{Relative draw-out force} = \frac{\text{Draw-out force of the self-reinforced rod } (N)}{\text{Draw-out force of the non-reinforced rod } (N)}$$

By measuring the draw-out forces to five self-reinforced and five non-reinforced threaded rods, an average of 1.4 was obtained for the relative draw-out force of self-reinforced, threaded rods. A screw-threaded rod of self-reinforced material implanted in the bone was thus significantly better compared to an implant of non-reinforced material.

What is claimed is:

1. A entirely amorphous resorbable material that resorbs after implantation into a patient comprising: an entirely amorphous material that is mechanically modified to reinforce the material by molecularly orienting the material, resulting in the material having increased shear and bending strength, wherein the material remains amorphous after being mechanically modified, and further wherein the material comprises a thermoplastic polymer, copolymer, polymer alloy, or combinations thereof.

2. The material as set forth in claim 1, wherein the material is mechanically modified uni-axially, by drawing.

3. The material as set forth in claim 1, wherein the material is mechanically modified bi-axially, by drawing.

4. The material as set forth in claim 1, wherein the material is mechanically modified by rolling, compression or shear transformation, combined with drawing, or performed separately.

5. A surgical implant formed from the material of claim 1, said implant having a longitudinal axis, wherein the molecular orientation of the material is parallel with said longitudinal axis.

6. A surgical implant manufactured from the material of claim 1, said implant having a shear strength greater than 60 MPa.

7. A surgical implant manufactured from the material of claim 1, said implant having a bending strength greater than 130 MPa.

8. The material as set forth in claim 1, wherein said material is poly-L/DL-lactide.

9. A method for manufacturing the material of claim 1, comprising the steps of:

selecting a starting composition from a group of entirely amorphous resorbable, thermoplastic polymers, copolymers, or polymer alloys, and mechanically modifying the material to molecularly orient and reinforce the material, yielding the molecularly oriented, reinforced material of claim 1.

10. The method as set forth in claim 9, further comprising the step of:

forming the material into a surgical implant having a longitudinal axis, wherein the molecular orientation of the material is substantially parallel to the longitudinal axis of the implant.

11. The method as set forth in claim 9, wherein said material of said starting composition is mechanically modified uni-axially or bi-axially.

12. The method as set forth in claim 9, further comprising the step of:

forming the material into a surgical implant having a longitudinal axis, wherein the molecular orientation of the material is substantially twisted, threaded or spiral in relation to the longitudinal axis of the implant.

13. A surgical implant formed from the material of claim 1, said implant having a longitudinal axis, wherein the molecular orientation of the material is twisted, threaded or spiral in relation to said longitudinal axis of the implant.

14. The material as set forth in claim 1, wherein said material is a copolymer of lactide and glycolide.

15. The material of claim 14, wherein said material is formed into a rod, screw, pin, hook, nail, plate, bolt, suture anchor, foils, wire, tube, stent or spiral for use as a resorbable, surgical implant in a patient.

16. The material of claim 8, wherein said material is formed into a rod, screw, pin, hook, nail, plate, bolt, suture anchor, foils, wire, tube, stent or spiral for use as a resorbable, surgical implant in a patient.

17. An entirely amorphous resorbable material that resorbs after implantation into a patient comprising:

an entirely amorphous material that is drawn to reinforce the material by molecularly orienting the material, resulting in the material having increased shear and bending strength, wherein the material remains amorphous after being drawn.

18. The material of claim 17, wherein the material is a thermoplastic polymer, copolymer, polymer alloy, or combinations thereof.

19. The material of claim 18, wherein the material is poly-LDL-lactide.

20. The polymer of claim 17, wherein the material is uni-axially or bi-axially drawn.

21. A surgical implant formed from the material of claim 17, wherein the orientation of the drawn material is parallel to a longitudinal axis of the implant.

22. A surgical implant manufactured from the material of claim 17, having a shear strength of greater than 60 MPA.

23. A surgical implant manufactured from the material of claim 17, having a bending strength greater than 130 MPA.

* * * * *